United States Patent [19]

Elliott et al.

[11] 3,954,808

[45] May 4, 1976

[54] METHYLENE BIS-PHENOL ALKANOIC ACID COMPOUNDS

[75] Inventors: John Scotchford Elliott; Bryan Terence Davis; Richard Martin Howlett, all of Bracknell, England

[73] Assignee: Edwin Cooper & Company Limited, Bracknell, England

[22] Filed: Nov. 1, 1973

[21] Appl. No.: 412,027

[30] Foreign Application Priority Data

Nov. 2, 1972 United Kingdom............... 50642/72

[52] U.S. Cl.................... 260/343.2 R; 252/48.6; 252/57; 260/343.3 R; 260/470; 260/473 S
[51] Int. Cl.²................ C07D 307/78; C07C 63/52; C07D 311/02
[58] Field of Search............ 260/473 S, 470, 343.3, 260/343.2 R

[56] References Cited
UNITED STATES PATENTS

| | | | |
|---|---|---|---|
| 2,789,995 | 4/1957 | Johnston............................ | 260/473 |
| 2,907,743 | 10/1959 | Greenlee............................ | 260/473 |
| 2,907,744 | 10/1959 | Greenlee............................ | 260/473 |
| 2,933,472 | 4/1960 | Bader................................. | 260/473 |
| 2,933,520 | 4/1960 | Bader................................. | 260/473 |
| 2,971,025 | 2/1961 | Bader................................. | 260/520 |

FOREIGN PATENTS OR APPLICATIONS

| | | | |
|---|---|---|---|
| 1,093,377 | 11/1960 | Germany........................... | 260/473 |

*Primary Examiner*—James A. Patten
*Attorney, Agent, or Firm*—Donald L. Johnson; Robert A. Linn; Joseph D. Odenweller

[57] ABSTRACT

Novel compounds, useful as intermediates in the preparation of lubricant additives, are described by specified general formulae and as condensation products of (i) an alkyl-substituted monohydric phenol, phenol sulphide or alkylene bis-phenol in which the alkyl substituent contains at least 8 carbon atoms and (ii) a carbonyl-substituted compound selected from the group consisting of glyoxylic acid, pyruvic acid, levulinic acid, 3-oxoglutaric acid, 2-oxoglutaric acid and esters of such acids.

7 Claims, No Drawings

METHYLENE BIS-PHENOL ALKANOIC ACID COMPOUNDS

This invention relates to lubricant additives, more particularly to certain novel compounds useful in the preparation of lubricant additives.

Amongst the numerous types of additives used in blending lubricants, particularly but not exclusively automotive lubricants, are various surface active materials. For example dispersants, particularly ashless dispersants, are incorporated in lubricants in order to disperse carbon particles and other insoluble materials such as decomposition products and fuel oxidation products in the oil medium which is the major constituent of the lubricants. The insoluble materials are thus suspended in the oil medium and prevented from forming deposits which can deleteriously affect engine operation. Another role in which surface active materials are used is in overbasing processes in which a suspension or dispersion of a metal compound, particularly an alkaline earth metal compound such as calcium, barium or magnesium oxide or hydroxide, is treated with an acidic gas such as carbon dioxide. During such processes a surface active material, commonly termed a soap, is used to form a stable suspension of the metal, for example in the form of the carbonate, in the resulting additives. The additives are basic, often very highly basic with total base numbers of up to 400 or 500 mg. KOH/g. and even higher, and are used to neutralise acidic combustion products formed in the engine.

Among the surface active materials used for the foregoing purposes are various alkyl salicylic acid derivatives. We have now found certain novel compounds which have some points of similarity in chemical structure to the known salicylate derivatives and which are useful in the field of lubricant additives.

Accordingly, the present invention provides a compound which is a condensation product of (i) an alkyl-substituted monohydric phenol, phenol sulphide or alkylene bis-phenol in which the alkyl substituent contains at least 8 carbon atoms, and (ii) a carbonyl-substituted compound selected from the group consisting of glyoxylic acid, pyruvic acid, levulinic acid, 3-oxoglutaric acid, 2-oxoglutaric acid and esters of such acids. The term monohydric phenol includes monohydric phenols having an alkyl substituent additional to that alkyl substituent containing at least 8 carbon atoms hereinbefore specified.

In another aspect of the invention there is provided a compound having the general formula:

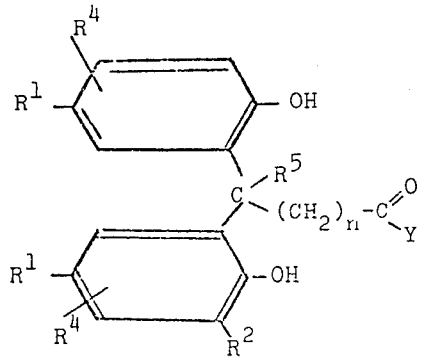

(A)

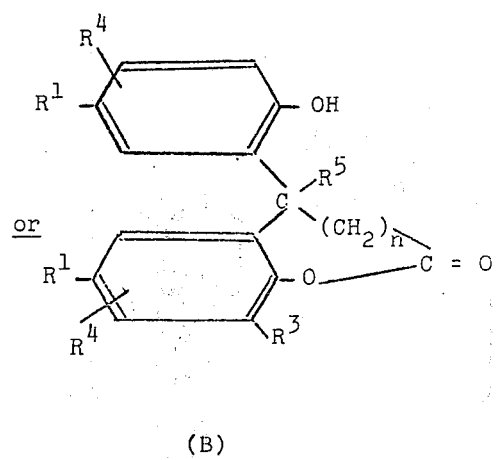

(B)

wherein each $R^1$ is the same or different and is an alkyl group containing at least 8 carbon atoms; $R^2$ is absent or is a group of the formula:

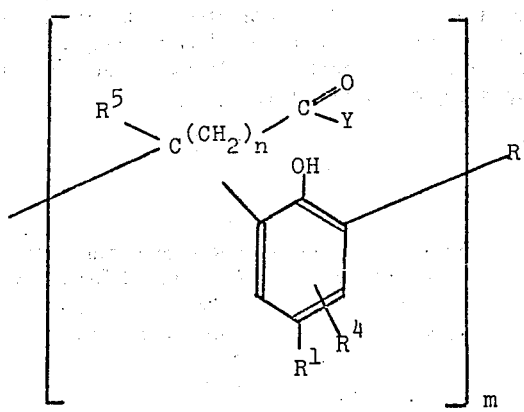

in which $m$ is zero or is an integer; $R^3$ is absent or is a group of the formula:

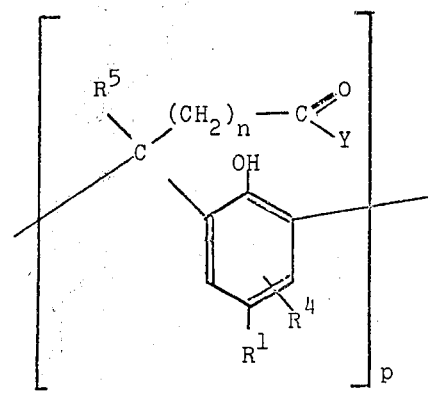

(C)

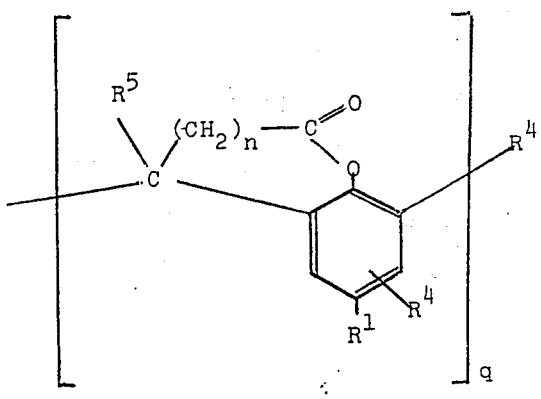

in which $p$ and $q$ are the same or different and are zero or are integers; each $R^4$ is the same or different and is absent or is a group of the formula $-Z-R^6$ in which Z is a sulphur atom or a chain of two or more sulphur atoms or is absent and $R^6$ is an alkyl group or an hydroxy-substituted aryl, aralkyl or alkaryl group; each $R^5$ is the same or different and is a hydrogen atom, a methyl group or the group $-(CH_2)_n$

each $n$ is the same or different and is zero or an integer of from 1 to 2; and each Y is the same or different and is a hydroxyl or alkoxy group. It is to be understood that in the case where $R^3$ is a group of the formula (C), the groups

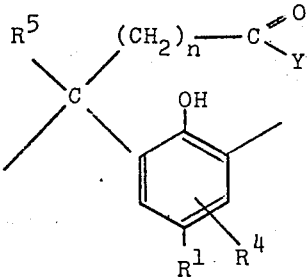

and

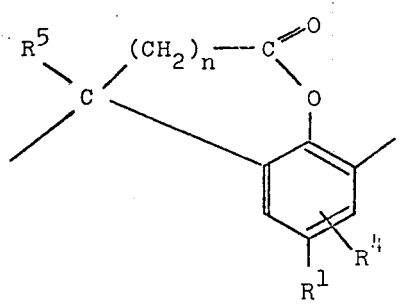

may be arranged in any order. For example, these groups may be randomly interspersed with each other and a block arrangement is not necessary.

The groups $R^1$ in the compounds of foregoing formulae (A) and (B), or in the case of the above-defined condensation products the alkyl groups derived from the alkyl-substituted moohydric phenol, phenol sulphide or alkylene-bis phenol may be comparatively short chain alkyl groups such as octyl, nonyl or dodecyl groups. Alternatively, these alkyl groups may be comparatively long chain groups containing at least 30, preferably at least 50, carbon atoms. However, to provide the desired degree of oil-solubility it is necessary that the number of carbon atoms in each of these alkyl groups is at least 8. To provide the desired dispersant properties the alkyl groups preferably contain at least 18 carbon atoms and for this reason the comparatively long chain alkyl groups are preferred. In this embodiment the alkyl groups may contain, for example, from 50 to 200 carbon atoms. In such cases the alkyl groups may be derived from long chain olefins such as a poly-(alphaolefin), which may have molecular weights in the range of 700 to 3,000, more preferably 900 to 1,500 and particularly about 1,000. Examples of suitable poly-(alphaolefins) are polyisobutylenes and polypropylenes.

In the case of the above-defined condensation products the alkyl-substituted phenolic starting material may bear one or more additional substituents on the aromatic ring and these correspond to the groups $R^4$ in the compounds of the foregoing formulae (A) and (B). When no substituent, other than the alkyl substituent, is present this corresponds to $R^4$ being a hydrogen atom. The alkyl substituent is preferably in the para-position corresponding to $R^1$ in formulae (A) and (B). Any other substituents are preferably positioned such that at least one ortho-position is unsubstituted, so that the phenol may be condensed with the carbonyl compound at this position and thereby phenol residues are linked at the ortho-position as illustrated in formulae (A) and (B).

The groups $R^4$, or the substituents corresponding thereto in the case of the condensation products, may be absent or may be groups of the formula $-Z-R^6$ as hereinbefore defined. In a preferred embodiment of the invention $R^4$ is absent, that it to say the $R^4$ "substituents", or corresponding "substituents" in the case of the condensation products, are hydrogen atoms. Such substances can be derived from alkylphenols having no substituent other than the alkyl substituent. In another embodiment the groups $R^4$, or corresponding substituents in the case of the condensation products, are present as groups of the formula $-Z-R^6$ in which Z is absent or is a sulphur atom or a chain of two or more, preferably 2 to 4, sulphur atoms. When Z is absent in this embodiment $R^6$ is an alkyl group, such as a short chain alkyl group containing 1 to 8, more preferably 1 to 4, carbon atoms or $R^6$ is a group of the formula:

in which $R^7$ is a hydrogen atom or an alkyl group and $R^8$ is an aryl or alkaryl group containing at least one hydroxy substituent. Conversely, when Z is a sulphur atom or a chain of two or more sulphur atoms in this embodiment, $R^6$ is preferably an aryl or alkaryl group which bears a hydroxy substituent.

The present invention also includes processes for preparing the novel substances. Accordingly, the invention includes a process wherein an alkyl-substituted monohydric phenol, phenol sulphide or alkylene bis-phenol in which the alkyl substituent contains at least 8 carbon atoms is condensed with a carbonyl-substituted compound selected from the group consisting of glyoxylic acid, pyruvic acid, levulinic acid, 3-oxoglutaric acid, 2-oxoglutaric acid and esters of such acids. In its preferred aspect the process comprises the condensation of an alkyl-substituted monohydric phenol, phenol sulphide or alkylene bis-phenol of the formula:

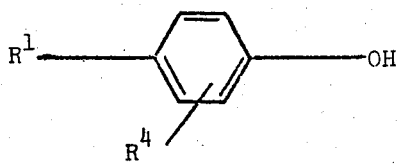

with a carbonyl-substituted compound of the formula:

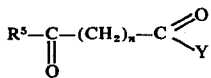

to form a compound of the formula (A) or (B), wherein $R^1$, $R^2$, $R^3$, $R^4$, $R^5$, n and Y have the same significance as hereinbefore defined.

In this process the product obtained is determined by the choice of reactants and the proportions employed. Thus the groups $R^1$ and $R^4$ are determined by the chosen phenolic reactant. For example, $R^1$ is determined by the alkyl substituent and products in which $R^4$ is absent can be prepared from phenolic reactants having no substituent other than the alkyl substituent. Similarly, products in which $R^4$ is present can be prepared from dialkylphenols (Z is absent and $R^6$ is an alkyl group); phenol sulphides (Z is sulphur or a chain of sulphur atoms); and alkylene bis-phenols (Z is absent).

When derived from phenol sulphides $R^6$ is a hydroxy-substituted aryl or alkaryl group, i.e. is a phenol residue or a phenol residue bearing an alkyl substituent (other than that corresponding to $R^1$ as hereinbefore described). When derived from alkylene bis-phenols $R^6$ is a hydroxy-substituted aralkyl group, that is a group of the formula

—CH—$R^7$
|
$R^8$ in which $R^7$ is a hydrogen atom or an alkyl group (preferably the former) as hereinbefore defined and $R^8$ is a phenol residue or a phenol residue bearing an alkyl substituent (other than that corresponding to $R^1$).

Likewise $R^5$, n, and Y are determined by the chosen carbonyl reactant. Thus products in which n is zero and Y is an hydroxyl group can be prepared from glyoxylic acid, pyruvic acid ($R^5$ is hydrogen and methyl, respectively). Alternatively, esters of such acids can be employed in order to vary the group Y. Similarly, products prepared from levulinic acid or esters thereof will provide compounds in which n is 2, $R^5$ being methyl. The use of 2- or 3-oxoglutaric acids or esters thereof will yield products in which $R^5$ is the group $(CH_2)_n$

for example acetonedicarboxylic acid (3-oxoglutaric acid) has the formula $O=C(CH_2-COOH)_2$ and will yield products in which $R^5$ is the group of $-CH_2-COOH$ and n is 1. Thus the carbonyl compound can be chosen to provide the desired products.

The groups $R^2$ and $R^3$ in the final products are determined by the proportions of the starting materials reacted together. Thus reaction of two moles of phenolic reactant with one mole of carbonyl compound yields products in which $R^2$ and $R^3$ are absent. Reaction of 3 moles of the phenol with two moles of carbonyl compound is necessary to provide compounds in which m is 1 and so forth. Thus the final product can be varied by varying the molar proportions of the starting materials reacted together. However, it is not necessary for the exact stoichiometric proportions of the reactants to be present during the condensation reaction.

The reactants used in the process of the present invention are in many cases commercially available materials, e.g. glyoxylic acid. The remainder may be readily prepared using well-known techniques; for example, poly(alphaolefin) substituted phenols may be prepared by alkylation of phenols with poly(alphaolefins).

The process of the present invention may be carried out under conditions varying over a wide range. For example, a temperature of from ambient temperature up to 150° C or even higher may be used. A preferred reaction temperature is from 60° to 120° C. Likewise, the pressure at which the condensation is carried out is not critical. Atmospheric pressure is convenient, but increased or reduced pressure may also be used. In a preferred embodiment of the process the condensation is carried out in an inert atmosphere, for example under a nitrogen blanket.

A highly desirable variation of the condensation is to carry out the reaction in an acid medium. This can be done by carrying out the reaction in the presence of an acid, for example, sulphuric acid, p-toluenesulphonic acid or a mixture of hydrochloric and glacial acetic acids.

In the case of an acid such as p-toluenesulphonic acid it is preferred to carry out the reaction at a comparatively high temperature, e.g. from 100° – 120° C or under reflux, this procedure being particularly effective when using glyoxylic or pyruvic acid or their esters as the carbonyl reactant. However, in the case of a mineral acid such as sulphuric acid a somewhat lower reaction temperature is preferred, e.g. 60° – 90° C and such a procedure has been found to be more effective with levulinic, 2-oxoglutaric and 3-oxoglutaric acids, and their esters.

An inert solvent may also be used if desired, examples of such solvents being benzene, chlorobenzene, toluene, xylenes, petroleum ether and mineral oil. Preferred solvents are those forming an azeotrope with the water produced in the condensation. The use of such solvents enables the water to be continually removed by azeotropic distillation during the course of the reaction. The term "solvent" used herein refers to a solvent for the phenol and carbonyl compound reactants. It is not necessary for the solvent to dissolve the acid when the condensation is carried out in an acid medium. For example, a very useful solvent/acid medium combination is petroleum ether and aqueous sulphuric acid. This combination provides a two-phase reaction system. However, single-phase reaction systems can also be used, a useful example of which is acetic acid dissolved in chlorobenzene. In the foregoing general formulae (A) and (B), compounds containing lactone rings as in (B) may be produced from the further condensation of phenolic hydroxyl groups with carboxyl groups derived from the use of a carbonyl-substituted carboxylic acid to form the internal cyclic ester. The products of the present invention may be used in the preparation of lubricant additives, for example, as described in our copending U.K. Pat. No. 19173/73.

The present invention will now be illustrated with reference to the following examples:

EXAMPLE I

Preparation of p-polyisobutylphenol 3340g. of 1000 m.w. polyisobutylene (Hyvis 10, ex B.P. Chemicals) was mixed with 2.4 litres of hexane. To the resulting solution was slowly added a complex/mixture of phenol and boron trifluoride which had been previously prepared by treating 846g. of molten phenol with 122g. of boron trifluoride. During the addition the reaction mixture was stirred under an atmosphere of nitrogen and maintained at 18°–20° C with external cooling. After completion of the addition the mixture was stirred at 18°–20° C for a further 3 hours. The boron trifluoride catalyst was precipitated from the mixture as ammonium fluoroborate by the addition of ammonium hydroxide (S.G. = 0.880) and removed by filtration. The solvent was then removed by distillation and the excess phenol removed by steam distillation. Titration of the phenolic hydroxyl group against tetra butyl ammonium hydroxide indicated the product to have an equivalent weight of 990.

EXAMPLE II

Reaction of p-nonylphenol with glyoxylic acid in the presence of p-toluene sulphonic acid A solution of nonylphenol (0.1m., 22g.) glyoxylic acid monohydrate (0.05m., 4.6g) and p-toluene sulphonic acid (0.3g.) in toluene (50 ml.) was heated at reflux temperature for 4 hours. Water evolved during the reaction was continuously removed by azeotropic distillation. The solvent was removed by distillation under reduced pressure. The product was a viscous deep red liquid, acidity = 116 mg. KOH/g.

EXAMPLE III

Reaction of p-polyisobutyl phenol with glyoxylic acid in the presence of p-toluene sulphonic acid The reaction was carried out by the same method as Example II using polyisobutyl phenol, as prepared in Example I, (0.09m., 89.1g.) glyoxylic acid monohydrate (0.06m., 5.5g.), p-toluene sulphonic acid (0.4g.) and toluene (100 ml.). The acidity of the product was 25 mg. KOH/g.

EXAMPLE IV

Reaction of polyisobutyl phenol with pyruvic acid in the presence of p-toluene sulphonic acid The reaction was carried out by the same method as Example II using polyisobutyl phenol, as prepared in Example I, (0.07m, 69.3g.), pyruvic acid (0.07m., 6.2g.), p-toluene sulphonic acid (1.0g.) and xylene (100 ml.). The acidity of the product was 5 mg. KOH/g.

EXAMPLE V

Reaction of p-polyisobutyl phenol with glyoxylic acid in the presence of sulphuric acid.

Polyisobutyl phenol, as prepared in Example I (0.3m., 297 g.) was dissolved in hexane (220 ml.). To the solution was added glyoxylic acid monohydrate (0.3 m., 27.6g.) and concentrated sulphuric acid (115ml.) diluted with water (54 ml.). The two phase mixture was then stirred and heated at reflux temperature (69° C) for 20 hours. After being diluted with further quantities of hexane and water, the mixture was allowed to stand until phase separation occurred. The hydrocarbon phase was then washed several times with water to remove sulphuric acid, dried over anhydrous magnesium sulphate, and stripped under reduced pressure to remove the solvent. The acidity of the product was 31 mg. KOH/g.

EXAMPLE VI

Preparation of p-polyisobutyl phenol 2100g. (1.0 mole) of 2100 m.w. polyisobutylene (Hyvis 150 ex B.P. Chemicals) were mixed with 1.7 litres of hexane. To the resulting solution was slowly added a complex/mixture of phenol and boron tri-fluoride which had been previously prepared by treating 254g of molten phenol with 37g. of boron trifluoride. The addition took 1½ hrs and the temperature rose from 22° to 27° C. The mixture was stirred for a further 3 hrs during which time the temperature rose a further 1° C. The boron trifluoride catalyst was precipitated from the mixture by addition of ammonium hydroxide (SG = 0.880). The precipitate and the excess phenol were removed by washing the hexane solution successively with 3.0, 2.0, 1.2 and 0.7 litres of aqueous/methanol (1:4). Finally the solvent was distilled off by vacuum stripping to 150° C. Titration of the phenolic hydroxide group against tetra butyl ammonium hydroxide indicated the product to have an equivalent weight of 2462.

EXAMPLE VII

Preparation of polypropyl phenol

The polypropylene used for the preparation was Amopol C60, ex Amoco Chemicals, molecular weight = 840.

The method used was as given in Example VI. The following ingredients were employed.

| | |
|---|---|
| Amopol C60 | 420g |
| $BF_3$ | 19g |
| Phenol | 126g |
| Hexane | 340ml |

-continued

| | |
|---|---|
| Aqueous/methanol(1:4) | 750 + 500 + 300 + 100ml |

Analysis indicated the product to have an equivalent weight of 2510.

EXAMPLE VIII

Preparation of polyisobutylo-cresol

O-cresol was alkylated with 1000mw polyisobutylene (Hyvis 10 ex B.P. Chemicals) by the method given in Example I.

The following ingredients were used:

| | |
|---|---|
| Hyvis 10 | 105g |
| O-cresol | 29.1g |
| $BF_3$ | 3.7g |
| Hexane | 50ml |

The solvent was removed by distillation and the excess o-cresol was removed by vacuum stripping to 200° C/5mm Hg.

Analysis indicated the product to have an equivalent weight of 1334.

EXAMPLES IX – XVII

Reaction of alkylphenols with glyoxylic acid in the presence of p-toluene sulphonic acid.

The reactions were carried out by the following general method, the details of the individual Examples being given in the Table.

A solution of the alkyl phenol, glyoxylic acid monohydrate and p-toluene sulphonic acid (PTSA) in solvent was heated at reflux temperature. Water evolved during the reaction was continuously removed by azeotropic distillation. When the evolution had ceased the solution was filtered and the solvent removed by distillation under reduced pressure. The products were generally deep red viscous liquids.

Examination of the quantities of water evolved in these preparations suggested that the carboxylic acid product was partially converted to the lactone form. This was also suggested by the acidity values, which were generally lower than the values calculated for the acid form. Infra red spectra contained a broad peak in the 1770–1820 $cm^{-1}$ region, suggesting a predominance of lactone.

The C14 – C18 phenol referred to in the Table was a commercial alkyl phenol mixture of average molecular weight of 460.

TABLE

| Ex. No | ALKYL PHENOL TYPE | MOLES | gm | PTSA gm | Glyoxylic Acid* MOLES |
|---|---|---|---|---|---|
| IX | Octylphenol | 0.5 | 103 | 0.2 | 0.25 |
| X | dodecylphenol | 0.3 | 78.4 | 1.0 | 0.3 |
| XI | dodecylphenol | 0.4 | 104.8 | 1.2 | 0.2 |
| XII | C14-C18 phenol | 1.0 | 460 | 1.1 | 1.0 |
| XIII | C14-C18 phenol | 1.0 | 460 | 1.0 | 0.5 |
| XIV | PIB phenol ex 1000 m2 PIB | 0.7 | 692 | 5.0 | 0.7 |
| XV | PIB phenol ex 2100 mw PIB | 0.05 | 123.1 | 0.1 | 0.025 |
| XVI | PIB o-cresol ex 1000 mw PIB | 0.05 | 66.7 | 0.1 | 0.025 |
| XVII | polypropyl phenol | 0.04 | 100.4 | 0.05 | 0.02 |

*Monohydrate - M.W. = 92

| Ex. No | SOLVENT TYPE | ml | WATER EVOLVED (ml.) found | calc for acid | calc for lactone | Acidity mg KOH/g. found | calc for acid |
|---|---|---|---|---|---|---|---|
| IX | xylene | 100 | 12.6 | 9.0 | 13.5 | 86 | 120 |
| X | toluene | 50 | 15.0 | 10.8 | 16.2 | 104 | 177 |
| XI | toluene | 50 | 11.0 | 7.2 | 10.8 | 65 | 97 |
| XII | 80/100 pet ether | 200 | 44.0 | 36.0 | 54.0 | 93 | 109 |
| XIII | 80/100 pet ether | 200 | 22.0 | 18.0 | 27.0 | 51 | 55 |
| XIV | toluene | 500 | 34 | 25.2 | 37.8 | 40 | 54 |
| XV | toluene | 70 | 1.0 | 0.9 | 1.4 | 14 | 11 |
| XVI | xylene | 60 | 1.1 | 0.9 | 1.4 | 14 | 21 |
| XVII | toluene | 65 | 1.0 | 0.7 | 1.1 | 15 | 11 |

EXAMPLE XVIII

Reaction of nonyl phenol with pyruvic acid

The reaction was carried out by the same method as Example II using the following ingredients:

| | | |
|---|---|---|
| nonyl phenol | 0.1m. | 22.0g. |
| pyruvic acid | 0.1m. | 8.8g. |
| PTSA | | 0.5g. |
| toluene | | 75ml. |

2.9 ml. of water was collected and the product had an acidity of 28 mg. KOH/g. Infra-red analysis showed strong absorption, believed to be due to a lactone function, in the range 1820–1770 $cm^{-1}$.

EXAMPLE XIX

Reaction of dodecyl phenol with pyruvic acid

The reaction was carried out by the same method as Example II using the following ingredients.

| | | |
|---|---|---|
| dodecyl phenol | 0.9m. | 235.8g. |
| pyruvic acid | 0.4m. | 35.2g. |
| PTSA | | 0.3g. |
| xylene | | 200ml. |

9.3 ml of water was collected and the product had an acidity of 21 mg. KOH/g.

EXAMPLE XX

Reaction of dodecyl phenol with 2-keto glutaric acid

To a mixture of dodecyl phenol (0.1m., 26.2g.), 2-keto glutaric acid (0.05m., 7.3g.), hexane (20ml.) and water (9ml.) was slowly added, with stirring and cooling, concentrated sulphuric acid (36ml.). This mixture was then stirred at room temperature for 65 hrs. It was then diluted with ethyl acetate and the ethyl acetate layer washed three times with water. Removal of the solvent by distillation under reduced pressure gave a viscous product with an acidity of 94 mg. KOH/g.

Infra-red analysis showed the expected absorption at 1710 cm$^{-1}$, due to an acid function and 1780–1810 cm$^{-1}$, due to a lactone function.

EXAMPLE XXI

Reaction of dodecyl phenol with acetone dicarboxylic acid

| | | |
|---|---|---|
| dodecyl phenol | 0.1m. | 26.2g. |
| acetone dicarboxylic acid | 0.1m. | 14.6g. |
| hexane | | 20ml. |
| water | | 9ml. |
| conc. sulphuric acid | | 36ml. |

The method was as given in Example XX except that in this case the reaction was carried out at 65° C for 13 hours.

A product of acidity 105 mg. KOH/g. was obtained and infra-red analysis showed the expected strong absorption at 1710 cm$^{-1}$ due to an acid function.

EXAMPLE XXII

Reaction of polyisobutyl phenol with acetone dicarboxylic acid

| | | |
|---|---|---|
| polyisobutyl phenol | 0.1m | 66.6g. |
| acetone dicarboxylic acid | 0.05m. | 7.3g. |
| hexane | | 50ml. |
| water | | 18ml. |
| conc. sulphuric acid | | 72ml. |

The polyisobutyl phenol was prepared from 440 m.w. polyisobutylene (Hyvis 07, ex B.P. Chemicals). by the method given in Example VI.

The reaction was carried out by the method given in Example XX, except that in this case the reaction time was    hrs. A viscous product of acidity 40 mg. KOH/g. was obtained and infra-red analysis showed the expected strong absorption due to an acid function at 1710 cm$^{-1}$.

EXAMPLE XXIII

Reaction of nonyl phenol with butyl glyoxylate.

A solution of nonyl phenol (0.3m., 66.0g.) butyl glyoxylate (0.15m., 19.5g.) and PTSA (0.1g.) in hexane (75ml.) was heated at reflux temperature. Water evolved during the reaction was continuously removed by azeotropic distillation. After 1½ hrs. 2.5 ml had been collected (calc. = 2.7ml.) and the evolution appeared to have ceased. The solution was then filtered and the solvent removed by distillation under reduced pressure at 30° C.

Infra-red analysis showed strong absorptions at 1715 cm$^{-1}$ and 1770–1820 cm$^{-1}$. (NB. The carbonyl absorption therefore that the desired condensation had taken place but that further reaction had then taken place to give a mixture of acid and lactone derivatives.

The acidity of the product was 66 mg. KOH/g.

The proposed reaction route is illustrated as follows:

[Reaction scheme: 2 phenol (OH, R) + CHO-CO$_2$Bu → intermediate with CO$_2$Bu bridge + H$_2$O → lactone and acid products]

A further preparation carried out in a higher boiling solvent, toluene, gave a product which only absorbed in the lactone region.

EXAMPLE XXIV

Preparation of bis dodecyl phenol sulphide.

[Reaction scheme: 2 phenol (OH, R) + 2 S →(NaOH) bis phenol sulphide + H$_2$S]

$$R = C_{12}H_{25}$$

A mixture of dodecyl phenol (1.0m., 262g.), sulphur (1.0m., 32g.) and caustic soda (8g.) was heated, with stirring, under nitrogen, at 160° C until the evolution of hydrogen sulphide ceased (42 hrs.). The caustic soda was neutralized with 10 ml. of phosphoric acid (SG =

1.75) and the mixture was then filtered. %S of Product = 5.85 (calc. = 5.8).

EXAMPLE XXV

Reaction of bis dodecyl phenol sulphide with glyoxylic acid

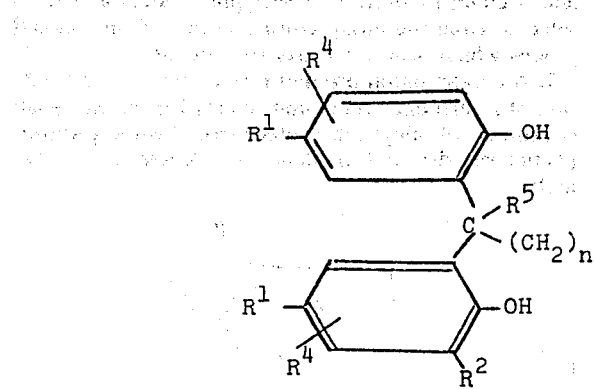

(A)

A solution of bis dodecyl phenol sulphide as prepared in Example XXIV (0.12m., 66.5g.), glyoxylic acid monohydrate (0.06m., 5.5g.) and PTSA (0.1g.) in xylene (50ml.) was heated at reflux temperature. Evolved water was continuously collected by azeotropic distillation. When 1.5ml. had been collected, the evolution appeared to have ceased and the solution was filtered and stripped of solvent. The product analysed as follows:

Acidity = 66 mg. KOH/g.
%S = 5.4 (calc. = 5.4)

Infra-red analysis showed a broad absorption at 1680 $cm^{-1}$ – 1820 $cm^{-1}$, the absorption being most intense at the acid region (1700 $cm^{-1}$) and the lactone region (1800 $cm^{-1}$)

EXAMPLE XXVI

Reaction of methylene bis dodecyl phenol with glyoxylic acid mono hydrate.

The reaction was carried out by the method given in Example XXV using the following ingredients.

| methylene bis dodecyl phenol | 0.08m. | 42.9g. |
|---|---|---|
| glyoxylic acid mono hydrate | 0.04m. | 3.7g. |
| PTSA | | 0.1g |
| xylene | | 50ml. |

1.9ml. of water was collected. The product gave an acidity of 70 and infra-red analysis showed the expected lactone absorption in the 1800 $cm^{-1}$ region.

We claim:
1. A compound having the general formula:

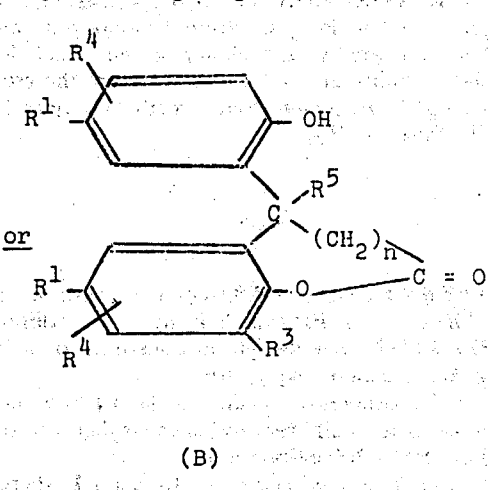

(B)

wherein each $R^1$ is the same or different and is an alkyl group containing at least 8 carbon atoms; $R^2$ is absent or is a group of the formula:

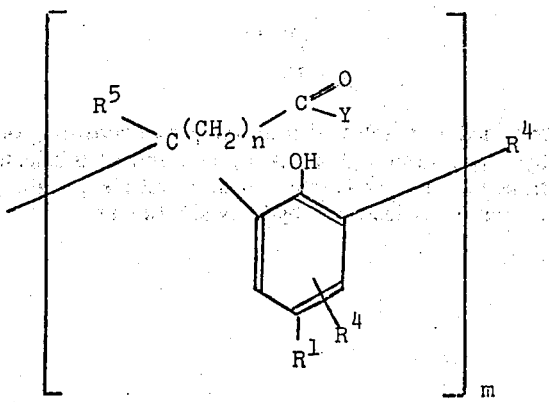

in which m is zero or is an integer; $R^3$ is absent or is a group of the formula:

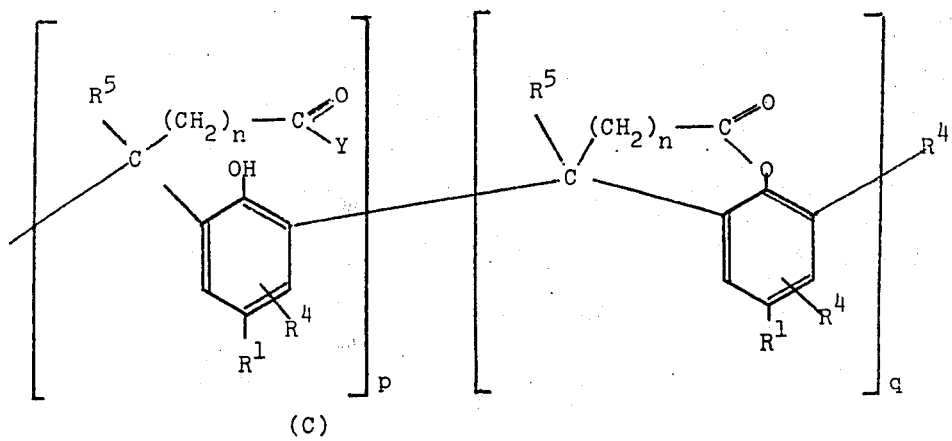

(C)

in which p and q are the same or different and are zero or are integers; each $R^4$ is the same or different and is absent or is a group of the formula $-Z-R^6$ in which Z is selected from the group consisting of a sulphur atom and a chain of at least two sulphur atoms or is absent and $R^6$ is selected from the group consisting of an alkyl group and hydroxy-substituted monocyclic hydrocarbon aryl, aralkyl and alkaryl groups; each $R^5$ is the same or different and is selected from the group consisting of a hydrogen atom, a methyl group and a group of formula $\{CH_2\}_n$

each n is the same or different and is zero or an integer of from 1 to 2; and each Y is the same or different and is selected from the group consisting of a hydroxyl group and an alkoxy group.

2. A compound according to claim 1 wherein each $R^1$ is the same or different and is an alkyl group containing from 50 to 200 carbon atoms.

3. A compound according to claim 1 wherein $R^1$ is derived from a poly-(alphaolefin) selected from the group consisting of polyisobutylene and polypropylene having a molecular weight in the range of 700 to 3000.

4. A compound according to claim 1 wherein Z is absent and $R^6$ is selected from the group consisting of an alkyl group and a group of the formula

in which $R^7$ is selected from the group consisting of a hydrogen atom and an alkyl group and $R^8$ is selected from the group consisting of aryl and alkaryl groups containing at least one hydroxy substituent.

5. A compound according to claim 4 wherein $R^6$ is a short chain alkyl group containing from 1 to 8 carbon atoms.

6. A compound according to claim 1 wherein Z is selected from the group consisting of a sulphur atom and a chain of from 2 to 4 sulphur atoms and $R^6$ is selected from the group consisting of aryl and alkaryl groups which bear a hydroxy substituent.

7. A condensation product formed by the condensation of a phenolic compound selected from the group consisting of alkyl-substituted monohydric phenols, phenol sulfides and alkylene bis-phenols of the formula:

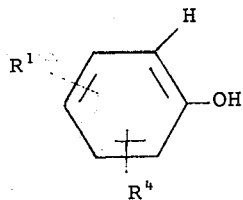

with a carbonyl-substituted compound selected from the group consisting of glyoxylic acid, pyruvic acid, levulinic acid, 3-oxoglutaric acid, 2-oxoglutaric acid and lower alkyl esters of such acids, wherein $R^1$ is an alkyl group containing at least 8 carbon atoms $R^4$ is hydrogen, or is a group of the formula $\{Z\}_r R^6$, where Z is sulfur and r is an integer of from 0 to 4; when r is 0, $R^6$ is $C_{1-8}$ alkyl or

where $R^7$ is hydrogen or an alkyl group and $R^8$ is a phenol or alkyl substituted phenol residue and when r is 1-4, $R^6$ is a phenol or alkyl substituted phenol residue.

* * * * *

UNITED STATES PATENT AND TRADEMARK OFFICE
CERTIFICATE OF CORRECTION

PATENT NO. : 3,954,808
DATED : May 4, 1976
INVENTOR(S) : John Scotchford Elliott et al It is certified that error appears in the above-identified patent and that said Letters Patent are hereby corrected as shown below:

Column 11, line 49 - insert -- 46 -- immediately preceding word "hrs."

Column 11, lines 67-68 - after "absorption" insert -- for butyl glyoxylate was found to be at 1760 $cm^{-1}$). It appeared --

Signed and Sealed this

Twenty-seventh Day of July 1976

[SEAL]

Attest:

RUTH C. MASON
Attesting Officer

C. MARSHALL DANN
Commissioner of Patents and Trademarks